US00PP23489P3

(12) United States Plant Patent
Baldwin

(10) Patent No.: US PP23,489 P3
(45) Date of Patent: Mar. 19, 2013

(54) ***MISCANTHUS* PLANT NAMED 'MSU-MFL1'**

(50) Latin Name: *Miscanthus×giganteus*
Varietal Denomination: MSU-MFL1

(75) Inventor: Brian S. Baldwin, Starkville, MS (US)

(73) Assignee: Mississippi State University, Mississippi State, MS (US)

( * ) Notice: Subject to any disclaimer, the term of this patent is extended or adjusted under 35 U.S.C. 154(b) by 0 days.

(21) Appl. No.: 12/932,823

(22) Filed: Mar. 7, 2011

(65) Prior Publication Data

US 2013/0025014 P1 Jan. 24, 2013

Related U.S. Application Data

(60) Provisional application No. 61/339,580, filed on Mar. 5, 2010.

(51) Int. Cl.
*A01H 5/00* (2006.01)

(52) U.S. Cl. ..... Plt./384

(58) Field of Classification Search ..... Plt./384
See application file for complete search history.

*Primary Examiner* — Annette Para
(74) *Attorney, Agent, or Firm* — Lawrence Arthur Schemmel

(57) ABSTRACT

*Miscanthus* plant 'MSU MFL1' is a new and distinct variety of giant *Miscanthus*, characterized by vigorous growth and its usefulness as an effective biomass grass that yields, on average, two to three times more tons per acre than switchgrass, the predominant biomass grass.

6 Drawing Sheets

STATEMENT OF GOVERNMENT SUPPORT

This invention was made with government support under 0209437 awarded by the Cooperative State Research, Education, and Extension Service, USDA. The government may have certain rights in the invention.

Latin name: *Miscanthus×giganteus.*

Varietal denomination: 'MSU MFL1'.

BACKGROUND OF THE INVENTION

This invention relates to the field of plants and more specifically to the field of giant *Miscanthus* plants and involves a new and distinct cultivar of giant *Miscanthus*, botanically known as *Miscanthus×giganteus* and referred to hereinafter by the name 'MSU MFL1'. The novel giant *Miscanthus* is a product of a planned breeding program conducted by the inventor at Starkville, Miss., to develop a new giant *Miscanthus* cultivar with good plant characteristics, vigorous growth habits, and large per acre yield. The species itself was derived from natural crossing in Japan of *Miscanthus sacchariflorus* (2n=4x) and *M. sinensis* (2n=2x), and the resulting hybrid is a seed sterile triploid (2n=3x).

The present invention, the new giant *Miscanthus* cultivar, is derived from parental material that was in the public domain (USDA ARS-GRIN, Miami, Fla.). Individual rhizomes/tillers were selected for the most vigorous growth (serial propagation) at Starkville, Miss. beginning in 2001 and further propagated by the inventor.

Asexual reproduction of the new cultivar 'MSU MFL1' by vegetative division/rhizomes has shown that the unique features of this novel plant are stable and reproduced true-to-type in successive generations.

SUMMARY OF THE INVENTION

The new and distinct cultivar of giant *Miscanthus* (*Miscanthus×giganteus*) designated 'MSU MFL1' has not been observed in or under all possible environmental conditions, so that the phenotype may vary with variations in environmental conditions such as temperature, daylength, light intensity, and moisture, for example, but without any variance in genotype. The new cultivar displays a vigorous growth habit, green leaves, and has excellent applicability as an efficient biomass grass plant.

The following traits have been repeatedly observed and represent the characteristics of the new cultivar. The botanical measurements presented in this disclosure were from three-year-old plants, which would be considered mature plants. The phenotype may vary somewhat with variations in temperature, daylength, light intensity, soil types, and water and fertility levels without, however, any variance in genotype. The following traits have been repeatedly observed and have been determined to be the basic characteristics of 'MSU MFL1', which in combination distinguish this *Miscanthus* hybrid from the known *Miscanthus×giganteus* and other ornamental *M. sinensis* forms:

1. Vigorous growth
2. Top leaf height about 9.0 ft=2.7 meters
3. Green leaves, no colored stripes are present
4. High biomass yield (about 9.93 dry ton/acre)
5. High tiller density 'MSU MFL1' can be distinguished from the *Miscanthus* cultivars 'Strictus' (not patented), 'Super Stripe' (U.S. Plant Pat. No. 18,161), 'Gold Bar' (U.S. Plant Pat. No. 15,193), 'Little Zebra' (U.S. Plant Pat. No. 13,008), and 'Mysterious Maiden' (U.S. Plant Pat. No. 16,197) in that 'MSU MFL1' has no stripes or colored bands on its leaves. More importantly, it can be distinguished from the all-green giant *Miscanthus* cultivars of 'Illinois' by leaf angle (28° for 'Illinois' vs. 32° for 'MSU MFL1') and of 'Nagara' (MBS 7001, U.S. Plant Pat. No. 22,033) by date of flowering (98% flowering for 'Nagana' on 19 August vs. for 'MSU MFL1' on 20 September at Starkville, Miss.).

DETAILED BOTANICAL DESCRIPTION OF THE VARIETY

Common name: Maidengrass, Chinese silvergrass.
Latin name: *Miscanthus×giganteus*.
Variety denomination: 'MSU MFL'.

The present invention is a novel *Miscanthus×giganteus* cultivar known as 'MSU MFL1' that is different from other giant *Miscanthus* cultivars. The following is a detailed botanical description of the characteristics of the new 'MSU MFL1' giant *Miscanthus* cultivar, based upon observations of the plant grown under natural conditions in Oktibbeha County, Miss.

Certain characteristics will vary depending on the age of the plants, such that characteristics such as dimensions, sizes, and/or colors are approximations or averages since the variety has not been observed under every possible environmental condition. Therefore, the variety may differ from the descriptions depending upon environmental variations including, but not limited to, the season, temperatures, daylength, light direction and quality, and fertilization, as well as other factors.

'MSU MFL1' is a seed sterile hybrid selected from naturally occurring variation in the crown of the original plant, and serially propagated vegetatively, selecting only the most vigorous vegetative tillers. The following botanical description is based on three-year-old, field grown plants.

General description: 'MSU MFL1' giant *Miscanthus* is a clump/bunch forming perennial grass.

Figure 1:
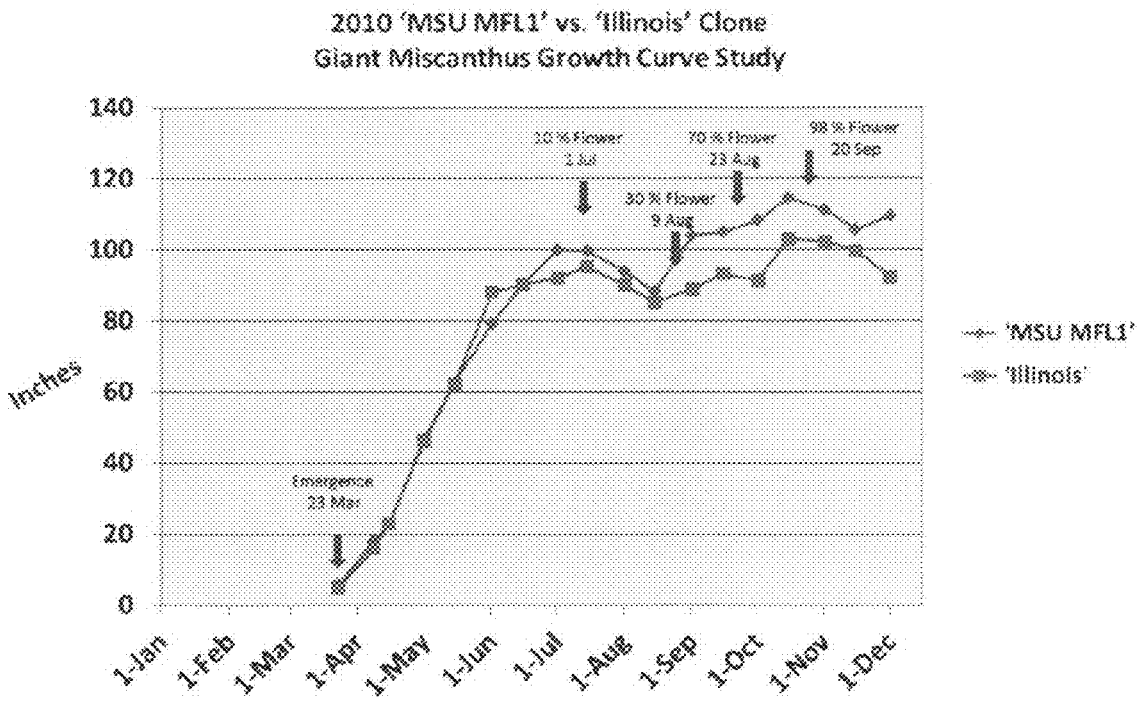
FIG. 1 is a graphical illustration of the 2010 growth curve study of the new 'MSU MFL1' giant *Miscanthus* and the 'Illinois' giant *Miscanthus* showing the differences between growth and significant flowering events of both cultivars at Starkville, Miss.

*Blooming period*.—At Starkville, Miss., inflorescence exert from boot starting in July. By 9$^{th}$ August, 30% of the plants are showing inflorescence. Peak bloom is achieved by the third week of September (FIG. 1). It should be noted that time of flowering is a function of rainfall and latitude. Plants grown farther north will flower later in the season than those in the southern part of the U.S.

*Height and spread*.—Top leaf height of 'MSU MFL1' is about nine feet at the end of the growing season (FIG. 1; Table 1a). This cultivar is generally taller than 'Illinois', but not significantly. Stem density does not differ from 'Illinois' (Table 1a). Circumference of crown increases rapidly until the third year, then slows dramatically, but culm number/density increases (Table 1b).

*Hardiness/latitudes of adaptation*.—Production and survival is similar to 'Illinois'. 'MSU MFL1' is generally no more and no less heat/cold/drought tolerant than 'Illinois', although it may be slightly less cold tolerant than 'Illinois'. The disease/insect resistance/susceptibility of 'MSU MFL1' is similar to 'Illinois'. Growth at: Ames, Iowa; Urbana, Ill.; and Starkville, Miss. show similar survival and onset of growth, though yields are different at Starkville for the two cultivars. Data reported from Syracuse, N.Y. indicated 'MSU MFL1' was slower to regrow in the spring (2012) than 'Illinois'. Production of giant *Miscanthus* in the southern U.S. is limited to areas north of Pensacola, Fla. (roughly 31° N latitude). South of that latitude, giant *Miscanthus* fails to grow sufficiently to warrant economic production.

*Culture/production*.—'MSU MFL1' grows best in fertile, well-drained sandy loam soils, such as those found in alluvial plains. This new plant does not tolerate standing water longer than two days during the growing season without significant stand reduction and corresponding reduction in yield. Higher yields are expected in warm temperate climates (southern Ohio, south to central Mississippi/Alabama). Early growing season water/rains are critical to maximum growth of 'MSU MFL1'. Production and regrowth is compromised in locations without sub-freezing temperatures.

*Root description*.—Fibrous and well-branched. Crown of the plant is composed of a dense mat of short rhizomes from which the roots arise. The subsequent year's growth arises in the spring from these rhizomes. Living rhizomes are beige in color. Active meristematic nodes are pink in color at their distal end.

*Stem description*.—The stem of 'MSU MFL1' is a cylindrical, erect monopodal, culm (hollow at maturity) with 12 nodes at Starkville, Miss. Stems are green in color and hairy during the growing season and become brown with the natural senescence of the crop in the fall (usually the end of October at Starkville, Miss.). Lower nodes are often pink to purple, similar to the distal tips of rhizomes. Most stems are green to gray-green (Munsell Color Chart 5G 6/2), but depending on location of the stem in the stand, stems exposed to sunlight often show reddish coloration (Munsell Color Chart 5R 8/2 to 5R 7/2).

*Stem size*.—Mean culm diameter is 7 mm with a mean of 12 leaves arising from corresponding nodes.

*Foliage description*.—Leaves are linear (blades), sheathed, simple acuminate with parallel venation. They are more or less uniformly green. Upper surface is green (Munsell Color Chart 2.5G 4/4 to 2.5G 5/4) and lower surface is green (Munsell Color Chart 7.5G 5/2). There is no variant coloration (white or yellow striping). Leaf blades are erect and concave at the proximal end becoming flat distally. Mean aspect of the mature leaf of 'MSU MFL1' is 32° vs. a mean aspect of 28° for 'Illinois' (Table 1a). Mean leaf width is 21 mm (just wider than 'Illinois'; Table 1a). Leaf length varies with climate and rainfall, but can be up to 700 mm.

*Flower and reproductive organ description*.—'MSU MFL1' flowers over a period of time from mid-July through late-September at Starkville, Miss. It flowers later in the season north of Starkville, Miss. and earlier in the season south of Starkville, Miss. Over five years of testing, viable seed production has never been observed. Its inflorescence is a collection of flowers that occur in a panicle which ranges in length from 25-35 cm and consists of an aggregate of racemes 20-25 cm long. Color varies based on aging and exposure to weather. Freshly emerging panicles are tan with brown cariopses. General inflorescence color is tan (Munsell Color Chart 2.5Y 8/2).

Figure 2:
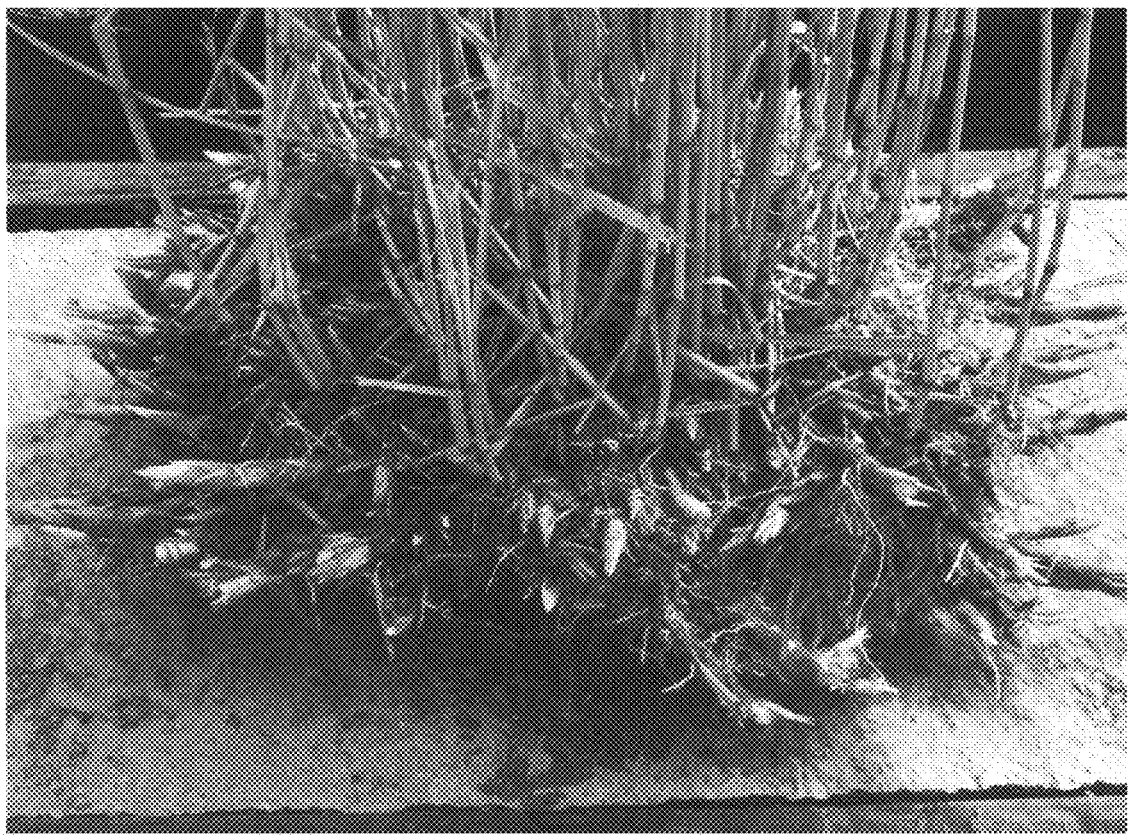
FIG. 2 is a color photograph of the 'MSU MFL1' cultivar showing its dormant crown with rhizomes.
Figure 3:
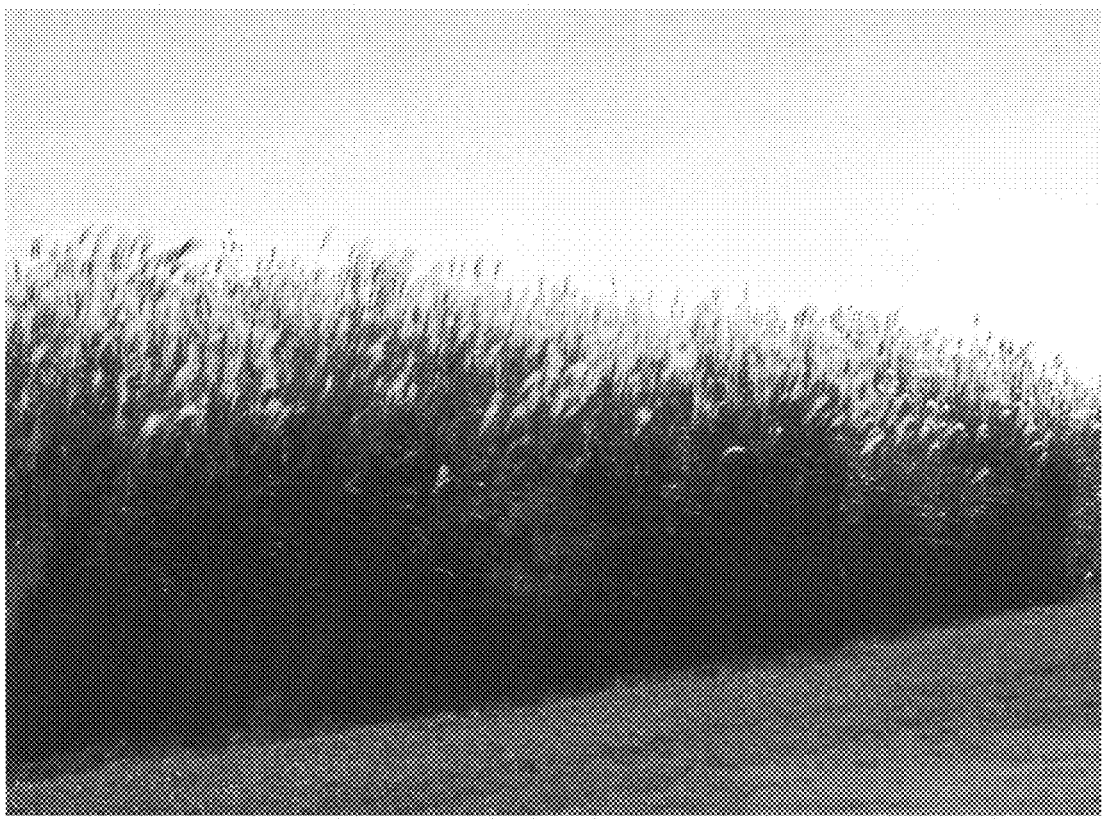
FIG. 3 is a color photograph of the 'MSU MFL1' cultivar parent block in full bloom at Starkville, Miss.
Figure 4:
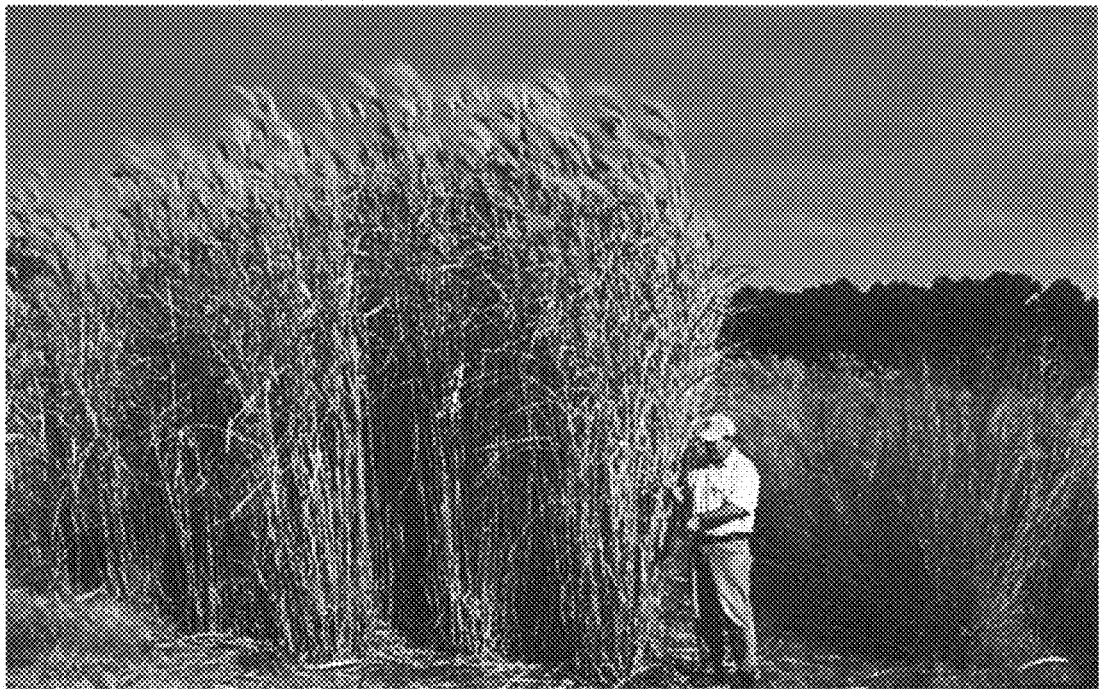
FIG. 4 is a color photograph of the height comparison of 'MSU MFL1' compared to switchgrass at Elsberry, Mo.
Figure 5:
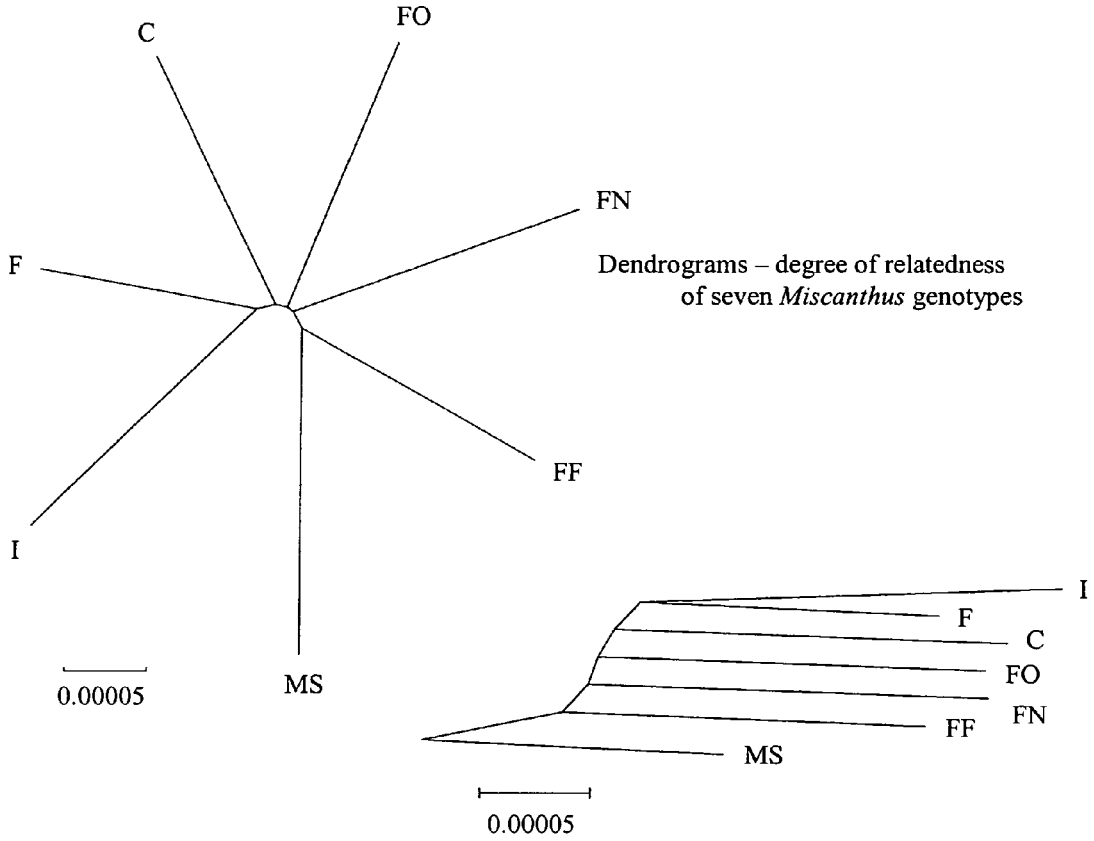
FIG. 5 is a pictorial representation of the dendograms for seven (7) *Miscanthus* genotypes, which includes the parents of 'MSU MFL1'.
Figure 6:
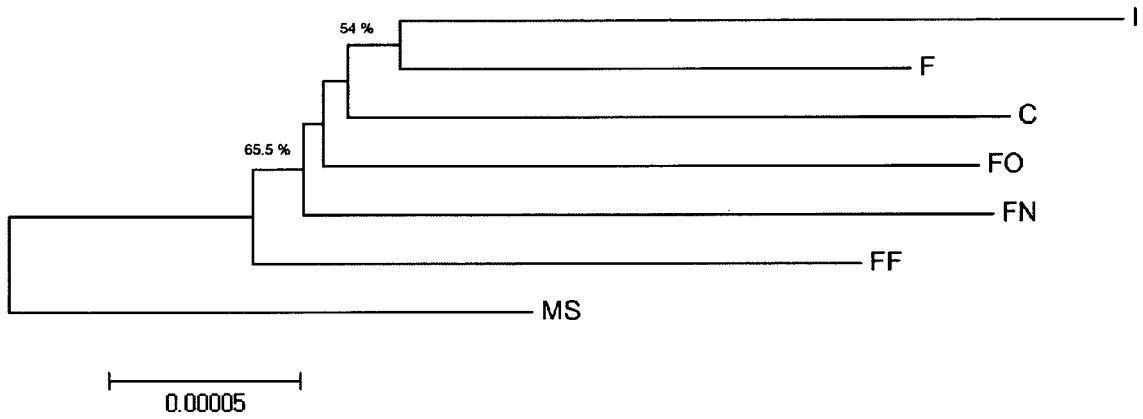
FIG. 6 is a pictorial representation of a phylogenetic tree that shows a linearized version of FIG. 5 and that 'MSU MFL1' is genetically different from the other giant *Miscanthus* cultivars analyzed.

The photograph of FIG. 1 shows the 2010 growth curve study of the new 'MSU MFL1' giant *Miscanthus* and the 'Illinois' giant *Miscanthus* clone, showing the differences between growth and significant flowering events of both cultivars at Starkville, Miss. The y-axis data of FIG. 1 represent height in inches. The photograph of FIG. 2 shows the new cultivar at its dormant crown with rhizomes. The photograph of FIG. 3 illustrates the parent block in full bloom and the overall appearance in a typical nursery field of the new giant *Miscanthus* cultivar 'MSU MFL1' grown in Starkville, Miss. The photograph was taken using conventional techniques and, although colors may appear different from actual colors due to light reflectance, it is shown as accurately as possible by conventional photographic techniques. The photograph and the detailed description of the invention are intended to illustrate further the invention and its advantages. The photograph of FIG. 4 shows the height comparison of the new cultivar 'MSU MFL1' compared to switchgrass at Elsberry, Mo. FIG. 5 shows dendograms for seven (7) *Miscanthus* genotypes, which includes the parents of 'MSU MFL1', where FF represents the 'MSU MFL1' field clone; FN represents the 'MSU MFL1' nursery clone; FO represents the 'MSU MFL1' original clone; I represents the 'Illinois' clone; C represents the commercially-purchased clone from Canada; F represents the commercially-purchased clone labeled *Miscanthus floridulus*; and MS represents the *Miscanthus sinisesis* genotype. FIG. 6 shows a linearized version of FIG. 5 and specifically a phylogenetic tree inferred by SNP analysis in common regions of all seven cultivar samples. Phylogeny is inferred using weighted SNPs/bp to prepare a distance matrix and to generate the neighbor-joining tree for the *Miscanthus* samples. FIG. 6 shows that 'MSU MFL1' is genetically different from the other giant *Miscanthus* cultivars analyzed. A previous AFLP-based approach (amplified fragment length polymorphism) was unable to demonstrate that sequence differences exist among giant *Miscanthus* cultivars that have been differentiated here. Based on the data, the following conclusions were made about the seven *Miscanthus* samples:

1. The 'MSU MFL1' plants FO, FF, and FN are more similar to each other than they are to 'Illinois'. On average 'Illinois' is 70% less similar to FO, FF, and FN than FO, FF, and FN are to each other.
2. The mRNA sequence data from FO, FF, and FN do not sequence identical. This could reflect differences in allele/homolog/paralog expression between the ostensibly genetically identical plants. However, the level of variation is very low, compared with the inter-cultivar or interspecies *Miscanthus* comparisons.
3. 'Canada' is related to 'Illinois' and the three 'MSU MFL1' varieties, but it is more similar to the three 'MSU MFL1' varieties than it is to 'Illinois'. 'Canada' is most similar to FO followed by FN and then FF.
4. F (the plant labeled *M. floridulus*) is related to all other plants in the analysis, but it groups more closely with the giant *Miscanthus* cultivars ('Canada', 'MSU MFL1', and 'Illinois') than it does with MS. Its similarity to giant *Miscanthus* indicates that F is most likely a mislabeled *Miscanthus*×*giganteus* plant.

The findings strongly suggest that multiple genotypes of giant *Miscanthus* are available. Genetic differences might account for observed differences in optimal growth region, disease resistance/susceptibility, and yield observed between giant *Miscanthus* cultivars. Planting a single genotype over a large geographic area increases susceptibility of the crop to catastrophic loss. The study indicates that the three giant *Miscanthus* cultivars studied ('MSU MFL1', 'Illinois', and 'Canada') are genetically different and that this diversity can be exploited in future cultivar development.

'MSU MFL1' *Miscanthus*×*giganteus* is a sterile hybrid of *M. sacchariflorus* and *M. sisensis*. The new cultivar 'MSU MFL1' was selected from germplasm that was identified by GRIN as *Miscanthus floridulus*, but has since been confirmed as giant *Miscanthus* (PI 295762). The most prevalent clone in the public domain is one available from Illinois ('Illinois' clone propagated from a plant growing at the Chicago Botanical Gardens). A secondary clone that entered variety trials in 2010 is designated 'Nagara' (U.S. Plant Pat. No. 22,033).

Rhizomes were obtained from the Plant Materials Repository in Miami, Fla. in 2001. Material obtained was originally thought to be *Miscanthus floridulus* 2x (and was incorrectly identified as such, PI 295762). Subsequent testing indicated that it was *M. giganteus*. Individual rhizomes were selected for vigorous growth of culms and serially propagated (a selection technique) in Starkville, Miss. (2001) and Stillwater, Okla. (2002). Serial propagation is a technique known in horticultural propagation that exploits slight somatic mutations that occur in the meristems of vegetatively propagated species. Since each new propagule arises from a single meristem, therefore whole plants can be selected that have that slight mutation. The main objective of serial propagation is to find material that is easier to propagate (usually rooting), but selecting new plants that establish and grow faster when planted was the inventor's goal.

Germplasm was originally obtained from USDA ARS-GRIN at Miami, Fla. (Tropical Crops Repository), whereby material was delivered in Spring, 2001. This material was field-planted and greenhouse propagated. Tillers that grew best (most vigorously) were selected for further propagation, a process known as serial propagation, which resulted in preferential amplification of material easier to propagate (and putatively result in slightly different genetics).

Samples were obtained from the three genotypes of what were identified by GRIN as *Miscanthus floridulus* in 2001, a listed synonym of *Miscanthus*×*giganteus*. Germplasm that performed the best at Starkville, Miss. is derived from PI 295762 (*M. floridulus* 2x). Individual rhizomes/tillers were selected for the most vigorous growth (serially propagated) at the Starkville, Miss. location starting in 2001. Individual tillers were propagated in what became known at the "3-Species test" (0.1 acre) and the "10-Species test" (0.05 acre). The "3-species test" was replicated at Stillwater, Okla. in June, 2002. A single plant was selected from the 3-Species test in 2005 and propagated by crown division without further selection pressure. All subsequent 'MSU MFL1' is derived from that single plant. The 10-Species test was destroyed to prevent contamination. The 3-Species test is still present at Starkville, Miss., but all material for propagation and distribution comes from a designated increase block.

The novel cultivar 'MSU MFL1' was selected from germplasm that was identified as *Miscanthus floridulus* by GRIN, but has since been confirmed as giant *Miscanthus* and different from the most prevalent clone in the public domain, the 'Illinois' clone (propagated from a plant growing at the Chicago Botanical Gardens).

The new plant has been tested at USDA ARS—Tifton, Ga.; USDA ARS—Temple, Tex.; USDA NRCS—Knox City; Tex., USDA NRCS—Elsberry, Mo.; University of Iowa, Ames, Iowa; University of Illinois; Oklahoma State University, Stillwater, Okla.; Mendel Biotechnology, Hayward, Calif.; and Sunbelt Biofuels, Soperton, Ga.

The parent material for this new cultivar was in the public domain (GRIN). Verification and re-verification of its unique nature was confirmed to be different from other varieties of giant *Miscanthus*. Two sources (Mendel Biotechnology and MSU-LSBI) confirmed that this cultivar was unique from other genotypes on the market or in the public domain (the 'Illinois' clone of giant *Miscanthus*). Moreover, research information indicated that this novel genotype 'MSU MFL1' is a seed sterile triploid and different from the original plant that was obtained from GRIN at Miami. Conventional wisdom initially suggested that there was only one clone of giant *Miscanthus* in the United States, the 'Illinois' clone. However, that information was not correct (Hodkinson et al., 2002).

'MSU MFL1' giant *Miscanthus* is a perennial, seed sterile triploid (2n=3x=57) that is propagated asexually via rhizomes and tillers. Rhizomes contain numerous stacked nodes with the terminal node resulting in large white spiked (or purple if exposed to light) tiller, which forms a primary shoot. Rhizomes proliferate between 0.5 and 2 ft of depth in the soil profile (Catalpa clay loam). Shoot growth is vigorous throughout the season, especially early in the season, with booting 100 days (1 July) after emergence (23 March), and heading 153 days (60% flowering; 23 August) after initial growth. Mature plants flower under long photoperiods, resulting in the formation of a compound spike inflorescence.

The new plants produce large amounts of dense dark green foliage with an alternate leaf arrangement and semi-hollow woody stems. Typical mature plants consist of heights ranging between eight and nine feet at Starkville, Miss., serrated leaves slightly greater than two feet in length with a prominent mid-vein, hair-like ligule, and contain dense plant crowns consisting of about 23 stems per $ft^2$. 'MSU MFL1' stems typically contain 12 nodes per plant and a stem diameter of seven millimeters. Morphological characteristics consistent with the new 'MSU MFL1' giant *Miscanthus* are similar to that of the *Miscanthus×giganteus* 'Illinois' clone cultivar, with the exception of leaf angle which is measured from above the node to the upper surface of the leaf. 'MSU MFL1' exhibits a standard mean leaf angle of 32°, while the 'Illinois' cultivar has a more acute leaf angle of 28° as measured from the vertical stem above the leaf. The initial expansion of the 'MSU MFL1' crown is faster than that of the 'Illinois' clone, giving the new 'MSU MFL1' a higher first year yield (see Tables 1a, 1b, 2a, and 2b; T/A=tons per acre).

TABLE 1a

Characteristics of 'MSU-MFL1' and 'Illinois' clone giant miscanthus.

| Cultivar | Mean Height (ft) | Mean Leaf Width (mm) | Mean Stem Density (per $ft^2$) | Mean Stem Dia. (mm) | Mean # Nodes/ plt | Leaf Angle (degrees) |
|---|---|---|---|---|---|---|
| 'MSU-MFL1' | 9.0 | 21 | 23 | 7 | 12 | 32 a† |
| 'Illinois' | 8.5 | 20 | 22 | 7 | 12 | 28 b |

Note:
†Numbers followed by the same letter are not significantly different at $\alpha = 0.05$. Data for comparison was generated from a side-by-side comparison of the 'MSU-MFL1' clone and the 'Illinois' clone planted at Starkville, MS. Means expressed above for morphological characters were calculated from five replicates of 20 stem samples. Lower case letters a and b denote statistical differences among varieties.

TABLE 1b

Rate of crown expansion of 'MSU-MFL1' giant miscanthus over four years.

| Crown Age (Months) | Mean CrownDiameter (ft) | Mean number of culms/crown |
|---|---|---|
| 12 | 3.06 | 26.6 |
| 24 | 4.08 | 51.8 |

TABLE 1b-continued

Rate of crown expansion of 'MSU-MFL1' giant miscanthus over four years.

| Crown Age (Months) | Mean CrownDiameter (ft) | Mean number of culms/crown |
|---|---|---|
| 36 | 5.08 | 74.2 |
| 48 | 5.53 | 300.1 |

TABLE 2a

Yield in US T/A comparing 'MSU MFL1' to 'Illinois' clone at Starkville, MS.

| Cultivar | Mean First Year Yield (T/A)* | Mean Second Year Yield (T/A) | Mean Third Year Yield (T/A) |
|---|---|---|---|
| 'MSU MFL1' | 5.42 a† | 7.53 a | 9.93 a |
| 'Illinois' | 4.04 b | 7.45 a | 8.30 b |

*Field is in its first full production year.
†Numbers followed by the same letter are not significantly different at $\alpha = 0.05$.
Yield was calculated from side-by-side testing, four replicates. Lowercase letters a and b denote statistical differences among varieties.

TABLE 2b

Yield in US T/A comparing 'MSU MFL1' to 'Alamo' switchgrass over the course of seven years at Starkville, MS.

| Species | 2003* | 2004 | 2005 | 2006 | 2007 | 2008 | 2009 |
|---|---|---|---|---|---|---|---|
| 'MSU MFL1' | 7.01 | 10.22 | 22.53 | 21.73 | 19.26 | 18.06 | 9.66 |
| 'Alamo' switchgrass | 5.7 | 9.60 | 16.90 | 17.23 | 11.30 | 10.53 | 8.18 |

*Field is in its first full production year.

The new cultivar, 'MSU MFL1', useful as an effective biomass grass, yields on average two to three times more than the predominant biomass grass switchgrass cultivar 'Alamo', at the same location. In a first year comparison of the 'Illinois' clone of giant *Miscanthus* and the new 'MSU MFL1', the 'Illinois' clone had a mean yield of 4.09 T/A (tons per acre) and 'MSU MFL1' had a mean yield of 6.76 T/A. Table 2b shows the yield in T/A (tons/acre) of 'MSU MFL1' compared to 'Alamo' switchgrass over a seven-year period at Starkville, Miss. It has been verified that the new cultivar is a genotype that is different from the material obtained from the public domain.

As will be apparent to those skilled in horticultural science, the new and distinct giant *Miscanthus* 'MSU MFL1' variety described herein may vary in minor detail due to climatic, soil, and cultural conditions under which the variety may be grown, as well as the stage of growth.

Genetic analysis indicates that the new cultivar is different from other known cultivars. Analyses were conducted by extracting mRNA from rhizomes of seven (7) different plants, converting the mRNA to cDNA, sequencing the cDNA using the Illumina Genone Analyzer, and comparing the sequence data set in silico. The decision to sequence mRNAs (cDNAs) was made since encoding sequences was expected to show the most sequence similarity because they are evolutionarily constrained by the function of the proteins they encode. Typically, there exists far less constraint on intergenic regions that exhibit more random nucleotide changes and are thus much less powerful for analysis groups of closely-related individuals.

Analyses were completed on over 400 million bases of cDNA sequence data from the seven (7) plants. The analyses focused on cDNA regions with high quality representation in all seven (7) species (4.7 million bases total) for SNP analysis. The SNP analysis was expected to be much more sensitive than AFLP or RFLP (restriction fragment length polymorphism) methods. The analysis determined that the 'Illinois' cultivar was on average 70% different than the cultivar 'MSU MFL1' (field, nursery, and original plants) than the 'MSU MFL1' plants were different from each other. FIG. 5 and FIG. 6 show the uniqueness of 'MSU MFL1' through dendrograms of seven (7) different *Miscanthus* genotypes.

The inventor can distinguish the new FF field clone 'MSU MFL1' from the existing FO original parent clone using singlenucleotide polymorphism (SNP) analysis on protein encoding sequences and has identified 2,387 specific SNPs that, out of 7,589,556 bases common between FF reads and FO, define the different genotype. This represents 0.03% of the sequence and, because it is coding sequence, includes many of the genetic changes that distinguish the FF phenotype from FO. These SNPs may be used to identify *Miscanthus×giganteus* clones as being more or less related to FO or FF.

What is claimed is:

1. A new and distinct cultivar of giant *Miscanthus, Miscanthus×giganteus* plant named 'MSU MFL1' substantially as herein illustrated and described.

* * * * *

FF= Freedom field; FN= Freedom nursery; FO=Freedom original clone; I=Illinois clone; C=commercially purchased clone from Canada; F=commercially purchased clone labeled *Miscanthus floridulus*; MS= *Miscanthus sinensis* genotype